United States Patent [19]

Pinkerton

[11] 4,197,196
[45] Apr. 8, 1980

[54] PROPORTIONING FLUIDS IN HEMODIALYSIS SYSTEMS

[76] Inventor: Harry Pinkerton, Bridle Path La., Mill Neck, N.Y. 11765

[21] Appl. No.: 687,133

[22] Filed: May 17, 1976

Related U.S. Application Data

[63] Continuation-in-part of Ser. No. 590,895, Jun. 27, 1975, abandoned.

[51] Int. Cl.$^2$ .................................. B01D 13/00
[52] U.S. Cl. ..................... 210/22 A; 210/321 B; 210/416 M
[58] Field of Search ............. 210/22, 321 B, 416 M; 128/214 E, 214 F, 214 K

[56] References Cited

U.S. PATENT DOCUMENTS

| | | | |
|---|---|---|---|
| 3,598,727 | 8/1971 | Willock | 210/22 |
| 3,844,940 | 10/1974 | Kopf et al. | 210/22 |
| 3,939,069 | 2/1976 | Grahger et al. | 210/22 A |
| 3,940,973 | 11/1976 | Boag et al. | 210/321 B |
| 3,979,284 | 9/1976 | Grahger et al. | 210/22 A |
| 4,093,545 | 6/1978 | Cullis | 210/86 |

OTHER PUBLICATIONS

McDonald, Jr., "An Automatic Peritoneal Dialysis Machine for Hospital or Home Peritoneal Dialysis: Preliminary Report", from vol. XV, Trans. Amer. Soc. Artif. Int. Organs, 1969, pp. 108–113.

*Primary Examiner*—Frank A. Spear, Jr.
*Attorney, Agent, or Firm*—Albert C. Nolte, Jr.; Edward B. Hunter

[57] ABSTRACT

In a hemodialysis system including a dialyzer having a semi-permeable membrane, apparatus for accurately proportioning and mixing fluids comprising a double acting piston/cylinder unit of which the cylinder is divided into two chambers by the piston and the volume of the cylinder swept by the piston at one end of the piston is lesser than that at the other end. An inlet connection for first liquid is made to one chamber, a conduit connects the two chambers and includes a connection to a source of the second liquid. Valve means are associated with the conduits and are effective to cause a charge of first liquid to be delivered to the one chamber and thereafter to be transferred to the other chamber, drawing liquid from the source of the second liquid to make up for the difference in volume. Said valve means then cooperate to cause the mixed liquids to be discharged from the other chamber as said one chamber is again charged with said first liquid. The apparatus is used for accurately establishing the rate of blood waste withdrawal from a patient and for the accurate proportioning and mixing of the liquids, namely, dialysate concentrate and dilution water, which constitute the component parts of dialysate solution.

In a variant the piston/cylinder unit is replaced by a receptacle divided by a flexible diaphragm into two chambers, the diaphragm flexing alternately to reduce the volume of one chamber as the other is expanded.

37 Claims, 4 Drawing Figures

PROPORTIONING FLUIDS IN HEMODIALYSIS SYSTEMS

REFERENCES TO RELATED APPLICATIONS

This application is a continuation-in-part of application Ser. No. 590,895 Filed June 27, 1975, now abandoned.

BACKGROUND OF THE INVENTION

This invention relates to improvements in hemodialysis systems and, more particularly, relates to improvements in such systems with regard to apparatus for accurately proportioning and mixing two liquids. According to one general aspect of the invention, improved means are provided for controlling the proportionate relationship between the dialysate solution and the waste material drawn from the blood of the patient across the membrane of a dialysis cell in the classical hemodialysis procedure and, by controlling the flow rate of the solution, establishing a desired waste withdrawal rate. According to another general aspect of the invention, improved means are provided for the accurate proportioning and mixing of the liquids, namely, dialysate concentrate and dilution water, which constitute the component parts of the dialysate solution.

In the practice of hemodialysis, it is essential to control the rate at which waste materials are withdrawn from the blood since adverse patient reactions are experienced from too slow a withdrawal rate as well as from too fast a withdrawal rate. Depending upon a patient's size, weight, age, activity level and general physical condition, waste withdrawal rates of 5 milliliters to 15 milliliters per minute are sought by dialysis practitioners. The withdrawal rate is conventionally manipulated by adjustment of the flow rate of the dialysate solution through the artificial kidney and by adjustment of the relative liquid pressure levels on the two sides of the semi-permeable membrane in the artificial kidney, liquid on the dialysate side of the membrane being maintained at pressure levels that are negative with respect to pressure levels on the blood size of the membrane.

A typical dialysis system would, for example, be arranged for a dialysate flow rate of approximately 500 milliliters per minute through the artificial kidney for an average waste withdrawal rate of 10 milliliters per minute, or 2%, i.e., a ratio by volume of 50 parts of dialysate to 1 part of waste fluid.

The prior art practices for attempting to control the rate at which the waste materials are withdrawn are inadequate. One technique has involved reliance on empirically derived charts based on such factors as the weight of the patient in order to determine the appropriate dialysate flow rate. This technique is notoriously unreliable. Another technique has involved utilization of a filled system in which dialysate overflow has been presumed to be attributable to waste withdrawal through the membrane. Splashing, bubbling, gasification and general turbulence introduce inaccuracies into this technique. Another technique has involved positioning a load cell under the patient's bed and observing the weight loss of the patient on the presumption that the weight loss directly represents the blood wastes drawn across the dialysis cell membrane. This technique is subject to external influences; for example, suppose that a nurse gives the patient a glass of water or an additional blanket and omits to inform the artificial kidney operator. The operator would observe a reduced withdrawal rate and would increase the fluid flow possibly to an extent to result in a dangerous withdrawal rate. Yet another technique involves measuring variations in the electrical properties of the dialysate to either side of the cell. This, however, is not a direct measure of waste withdrawal and, consequently, is subject to inaccuracies.

Another disadvantage of the prior art is that single patient dialysis systems require bulky tanks for batch mixing of dialysate solution or require extensive electrically driven pumping systems to mix dialysate solutions with the line water fed to the artificial kidney unit. Commercially available dialysate concentrate is typically mixed with line water in a ratio of one part concentrate to 34 parts water in such installations.

Apparatus utilized in hemodialysis procedures for mixing liquids in accurate proportions is shown in Willock's U.S. Pat. No. 3,598,727 issued Aug, 10, 1971. In that apparatus, a double acting piston/cylinder unit has a pair of piston rods which extend from opposite ends of the cylinder in which the first liquid (usually water) is handled and each one extends into a corresponding one of two cylinders connected to a supply of a second fluid (a dialysate concentrate). The liquids are delivered through a spool valve to be mixed before being admitted to a dialysis cell.

While Willock's apparatus may be accurate, it of course requires multiple piston and cylinder units and complex valving to unite the liquids.

BRIEF SUMMARY OF THE INVENTION

It is one object of the present invention to provide means by which the aforementioned ratio or any other arbitrarily selected ratio of dialysate flow rate to waste withdrawal rate may be maintained in the dialysis system regardless of the gross flow rate through the system and by which cumulative measures of the total withdrawal can be readily and accurately observed.

It is another object of the present invention to provide means for accurately mixing the concentrate and diluting water in a fixed ratio.

These objects are attained in the present invention by providing a proportioning and mixing device including a receptacle divided into two chambers by reciprocable partition means and means effective to produce reciprocation of said partition means alternately to expand and contract said chambers, in which a determined volume of a first liquid is delivered to one chamber during movement of the partition means in one direction and is transferred from that chamber to the other chamber during movement in the opposite direction, there being a connection from a supply of a second liquid into the system and means disposed in said one chamber effective to render the volume of first fluid transferred from said one chamber to said other chamber lesser than that required to fill said other chamber so that the difference in volume be made up by the second liquid. By the selection of appropriate component dimensions to form a specific difference in volume, a particular ratio of the liquids can be established and accurately maintained. When the apparatus is used to maintain a predetermined ratio of the dialysate volumetric flow rate to the volumetric waste withdrawal rate, the first liquid is dialysate solution and the second liquid is made up of the wastes withdrawn from the blood. When the apparatus is used in the preparation of the dialysis solutions, the first liquid is the water used to dilute the dialysate concentrate and the second liquid is the dialysate concentrate.

Optionally, means are provided for adjusting the quantity of second liquid admitted to the system.

BRIEF DESCRIPTION OF THE DRAWINGS

Embodiments of this invention are illustrated in the accompanying drawings, in which.

DESCRIPTION OF THE PREFERRED EMBODIMENTS

For purposes of clarity, only the essential elements of the invention are shown. Other commonly used hemodialysis components such as blood cell detectors, dialysate temperature control elements and electronic safety alarm and indicating components will be readily visualized by one skilled in the art.

Figure 1:
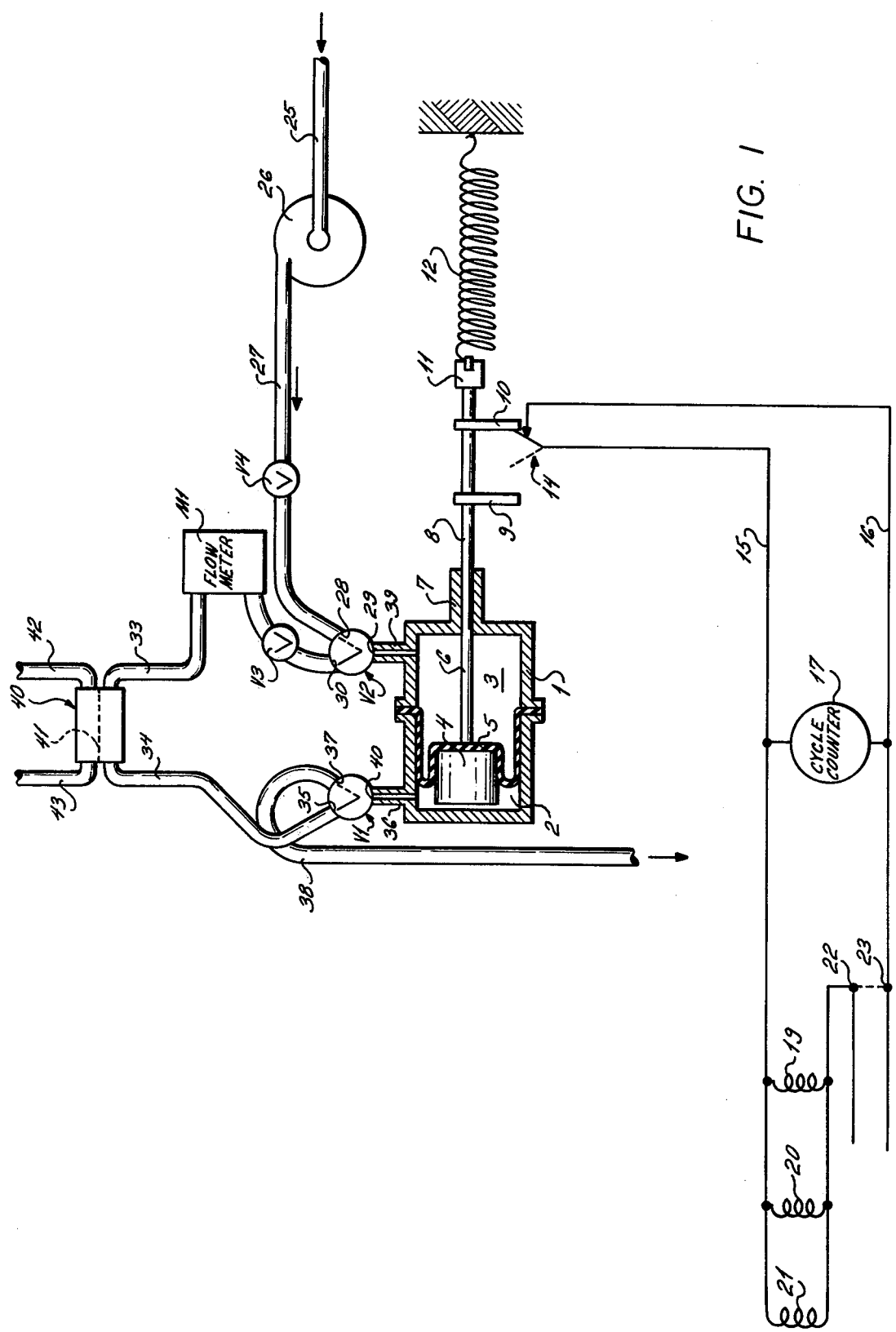
FIG. 1 shows, schematically, one embodiment of this invention.

The hemodialysis system of FIG. 1 includes proportioning means comprising a hydraulic circuit including the cylinder of a piston/cylinder unit 1 which is divided into chambers 2 and 3 by a piston unit 4 which has a rolling diaphragm 5. Extending from one end of the piston is a piston rod 6 guided in an extension 7 of an end wall of the cylinder.

The region 8 of the piston rod outside of the cylinder 1 is provided with adjustable stop means 9 and 10 which cooperate in a manner to be described hereinafter with a switch indicated generally at 14. Secured to the end of the piston rod at 11 is spring 12, the other end of that spring being fixed so that the spring is effective to bias the piston from left to right.

The switch 14 is included in a circuit 15, 16 which comprises a cycle counter 17, the purpose of which is described infra, coils 19 and 20 of solenoids associated with valves and motor 21 which drives the pump 26 as hereinafter described. A connection to an electrical supply is made at terminals 22 and 23.

An inlet 25 for the dialysate solution is made through centrifugal pump 26 to line 27 which includes a metering valve V4 which, as will be apparent from the following description, controls the velocity of right to left piston movement. From the metering valve V4, the line 27 extends to a first port 28 of a three port valve V2, through said valve V2 to common valve port 29 which is connected to cylinder port 39 leading to chamber 3 of cylinder 1.

A connection is made between chamber 3 of cylinder 1 and chamber 2 by means of cylinder port 29 and valve port 39 which have a common role as a part of the dialysate solution inlet and as part of the conduit connecting the two chambers of the cylinder, that latter conduit being completed through third port 30 in valve V2, a regulating valve V3, which controls left to right piston velocity, and line 33 to line 34, through a three port valve V1 and cylinder port 36. Lines 34 and 33 form the respective inlet to and outlet from the dialysate side of a dialysis cell 40 provided with a semi-permeable membrane 41. Blood from the patient is conducted to and from the other side of the membrane 41 in the cell 40 by respective conduits 42 and 43.

Conveniently, a flow mater M1 is disposed in the line 33 and the meter may be calibrated and read in units of flow rate for each of the dialysate solution stream and the waste material stream, since, of course, the two flow rates are directly related to each other in a fixed proportion.

An outlet conduit from chamber 2 is constituted by cylinder port 36 which, as is the case with cylinder port 39, has a common role as both an inlet to chamber 2 and as an outlet from that chamber, the outlet from chamber 2 being completed through valve V1 at port 37 to an outlet line 38.

The operation of the device of FIG. 1 is as follows:

As the piston 4 completes its stroke from right to left, the switch 14 will be thrown by the adjustable stop 10 causing de-activation of the solenoids in circuit 15/16 so that valves V1 and V2 will adopt the positions shown in full line at which time delivery of the dialysate solution to chamber 3 by pump 26 will be ceased as the electrical supply to motor 21 is interrupted, and the piston 4 will begin its movement left to right under the influence of spring 12. At this time, the fluid within chamber 3 will pass through valve V2, flow rate regulating valve V3, the flow meter and valve V1 to chamber 2 and, since the volume of chamber 3 is lesser than that of chamber 2, the excess fluid required to fill chamber 2 will be drawn into the system in the form of waste fluid across the membrane 41.

As the piston completes its left to right movement, stop 9 will activate switch 14 to cause the solenoids to shift the valves V1 and V2 to the position shown in chain line and motor 21 will be activated. At this time, the dialysate solution will be admitted to chamber 3 causing the piston to move from right to left and the fluid circuit between chambers 2 and 3 through valves V1 and V2 will be blocked, valve V1 making the connection between chamber 2 and outlet 38 so that the mixture of dialysate solution and waste material in chamber 2 passes to outlet line 38 to be discarded. Further, it will also be understood that, with the volumetric displacement of each piston stroke known for each of the two cylinder chambers 2 and 3 in the invention described in FIG. 1, cycle counter 17 provides the multiplier (cycles times stroke volume) to render conveniently visible the cumulative volume of said dialysate solution, blood wastes and the mixture passed to waste at any time during continuous operation of the system, during a typical hemodialysis procedure. Thus, while the facility for accurately reading instantaneous flow rate values is provided by flow meter M1, such values are arbitrarily adjustable through flow control valve V3, and the critical cumulative volume flow values, which may represent the difference between life and death for the hemodialysis patient, are continuously presented for surveillance by the operator of the dialysis system.

It will be appreciated that in the construction hereinabove described, the quantity of the waste liquid drawn into the chamber 2 is directly related to the difference in volume between the chambers 2 and 3 which in turn is directly related to the cross-sectional area of the piston rod 6, or at least that part of the piston rod within the chamber 3, and the stroke of the piston. Thus, by the careful selection of rod area to piston area ratios, one is able to establish a fixed proportion of the dialysate solution and waste liquid in the mixture which issues from outlet 48.

It is, of course, to be appreciated that the arrangement illustrated in FIG. 1 is a schematic and shows a particularly desirable system in which the dialysate solution inlet to one side of a cylinder and the interconnection between the two sides of the cylinder includes a common branch, i.e. valve port 29. Further, the interconnection between the two sides of the cylinder and the outlet from chamber 2 includes a common portion constituted by valve port 40 and cylinder port 36.

Additionally, while in the particular arrangement illustrated a single pole single throw toggle switch type arrangement has been illustrated, quite conceivably, and in some instances more desirably, that switch could be replaced by other switch means, as for example by photoelectric cells. Also, it will be recognized that at the ends of the stroke of the piston, a pressure surge will occur in the system and this may be utilized to effect control of the valves by the utilization of an appropriate sensor as for example a diaphragm element.

Clearly, too, the apparatus could be modified so that instead of relying upon the pressure of the delivery of the dialysate solution and the spring for movement of the piston, a positive mechanical drive could be applied to the piston with appropriate modifications of the piston to cylinder seals.

When the proportioning device of FIG. 1 is used to produce the dialysate solution by proportioning dialysate concentrate and dilution water, fluid inlet 25 would be supplied with dilution water, appropriately heated, filtered, pressurized and otherwise pretreated, and fluid inlet 32 would communicate with a reservoir of dialysate concentrate.

Figure 2:
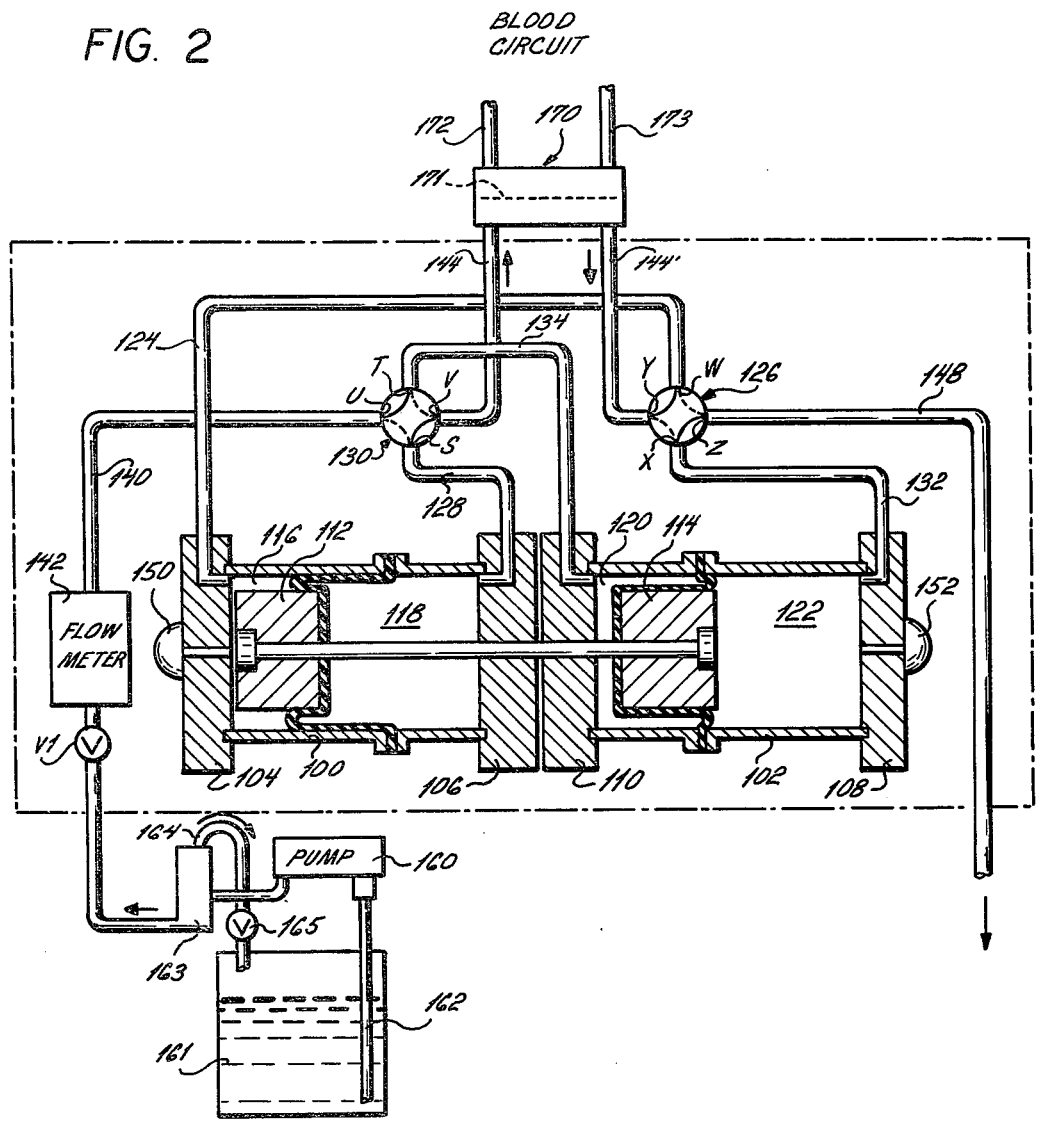
FIG. 2 shows, schematically, a further embodiment of this invention.

In FIG. 2 there is shown an arrangement, in many respects resembling that of FIG. 1, but in which there are two piston/cylinder units. To distinguish clearly between the embodiments of FIG. 1 and FIG. 2, parts of the apparatus of FIG. 2 are identified by different reference numerals from those utilized in the embodiment of FIG. 1.

The apparatus of FIG. 2 comprises a left hand cylinder 100 and a right hand cylinder 102. The ends of cylinder 100 are closed by port plates 104 and 106 and those of cylinder 102 are closed by port plates 108 and 110.

Disposed within cylinders 100 and 102 are pistons 112 and 114, respectively, each provided with a conventional rolling diaphragm seal so that cylinder 100 is divided into chambers 116 and 118 at opposite ends of the piston and cylinder 102 is divided into chambers 102 and 122 to each side of piston 114. It is to be noted that the pistons are joined by a common piston rod guided in port plates 106 and 110.

Leading from chamber 116 through port plate 104 conduit means 124 communicates with port W of a four port valve 126 and conduit 128 leads to port S of a four port valve 130 from chamber 118, through port plate 106.

Conduit 132 leads to port X of valve 126 from chamber 122 through port plate 108 and conduit 134 communicates between chamber 120 of cylinder 102 and port T of valve 130.

Dialysate solution is pumped by a pump 160 from a dialysate supply 161 through a conduit 162 and orifice chamber downstream from the pump 160 to a conventional deaerator 163, provided with an air return line having a valve 165, and therefrom to a fluid inlet conduit 140 which extends from the deaerator 163, through a flow meter 142 to port U of valve 130. Conduit 144 communicates between port V of valve 130 and the inlet of the dialysate side of a dialysis cell 170 provided with a semi-permeable membrane 171. At the other side of the membrane 171, blood is conducted from and back to the patient through respective conduits 172 and 173. Conduit 144' communicates with the outlet of the dialysate side of the dialysis cell 170 and port Y of valve 126.

The valve 126 also includes a port Z communicating with conduit 148 which leads to an outlet for the mixture of dialysate solution and waste fluid.

Disposed in port plates 104 and 108 are proximity switches 150 and 152, respectively.

The operation of the device of FIG. 2 is as follows:

In the position shown in the drawings, i.e., with the pistons at the extreme left of their respective cylinders, port U of valve 130 is connected to port T and port S is connected to port V. In valve 126, port Y is connected to port W and port X is connected to port Z.

It is to be appreciated that the position of the valves 126 and 130 is to be controlled by solenoids actuated by one or other of switches 150, 152 in this embodiment shown as proximity switches, but obviously any type of sensor compatible with the role of those switches may be used to control articulation of the valves of the system.

In the meantime, dialysate solution supplied under adequate pressurization to constitute the dialysate solution as a motive fluid for the piston system will be passed along conduit 140 through the flow meter 142 and flow rate regulator valve V1 to flow director valve 130 where it will move from port U to port T and through line 134 to chamber 120 of the cylinder 102.

Considering cylinder 100, as the piston 112 begins its movement from left to right, fluid contained in chamber 118 passes through ports S and V of valve 130, along conduits 144 and 144', through ports Y and W of valve 126 and along conduit 124 to chamber 116. Since the volume of fluid displaced from chamber 118 is lesser than that required to fill chamber 116, the difference in volume will be made up by the waste fluid drawn through the membrane 171 to the dialysate side of the dialysis cell 170 where it mixes with the dialysate solution and the mixture is conducted into conduit 144'.

At the same time, fluid in chamber 122 will be moved from that chamber to line 132 and via ports X and Z of valve 126 to line 148. It will be apparent from what follows that the fluid from chamber 122 will comprise a precise mixture of predetermined proportions of the dialysate solution and waste fluid.

As the pistons 112 and 114 approach the extreme right hand position, proximity switch 152 will be activated to cause appropriate solenoids, not shown in the drawings, to shift the positions of valves 126 and 130 so that the dialysate solution will pass along conduit 140 from port U to port S of valve 130 to enter chamber 118 providing the motive force to shift the pistons from right to left. Fluid in chamber 116, as described hereinbefore, a predetermined mixture of the dialysate solution and waste fluid, will be moved along conduit 124 to pass from port W to port Z of valve 126 and along outlet 148. Similarly, fluid in chamber 120 will be moved along conduit 134 to pass from port T to port V of valve 130 and along conduits 144 and 144' to pass from port Y to port X of valve 126 and along conduit 132, to chamber 122. Since the volume of that fluid is lesser than that required to fill chamber 122, the excess will be made up by the waste fluid drawn across membrane 171.

As the device continues to operate, a substantially constant flow of a mixture of predetermined proportions of dialysate solution and waste fluid will issue from line 148 to be discarded.

As with the apparatus of FIG. 1, it is to be appreciated that the structure of FIG. 2 is subject to various modifications which do not deviate from the scope of the invention as defined in the appended claims. For example, the pipe work exterior to the cylinders can be varied along with appropriate variations in the valving. Also, while in this particular embodiment utilization of proximity switches has been described, clearly those devices could be replaced by any other appropriate units as discussed hereabove.

The embodiment of FIG. 2 has been described with particular reference to its utilization to regulate the proportioning of the dialysate solution and the waste fluid withdrawn by the dialysate solution. In the use of such apparatus in the preparation of dialysis solutions from concentrate, the pumped fluid would be dilution water, appropriately heated, filtered, pressurized, diagnosed and otherwise pretreated, while the other fluid would be a dialysate concentrate material.

Figure 3:
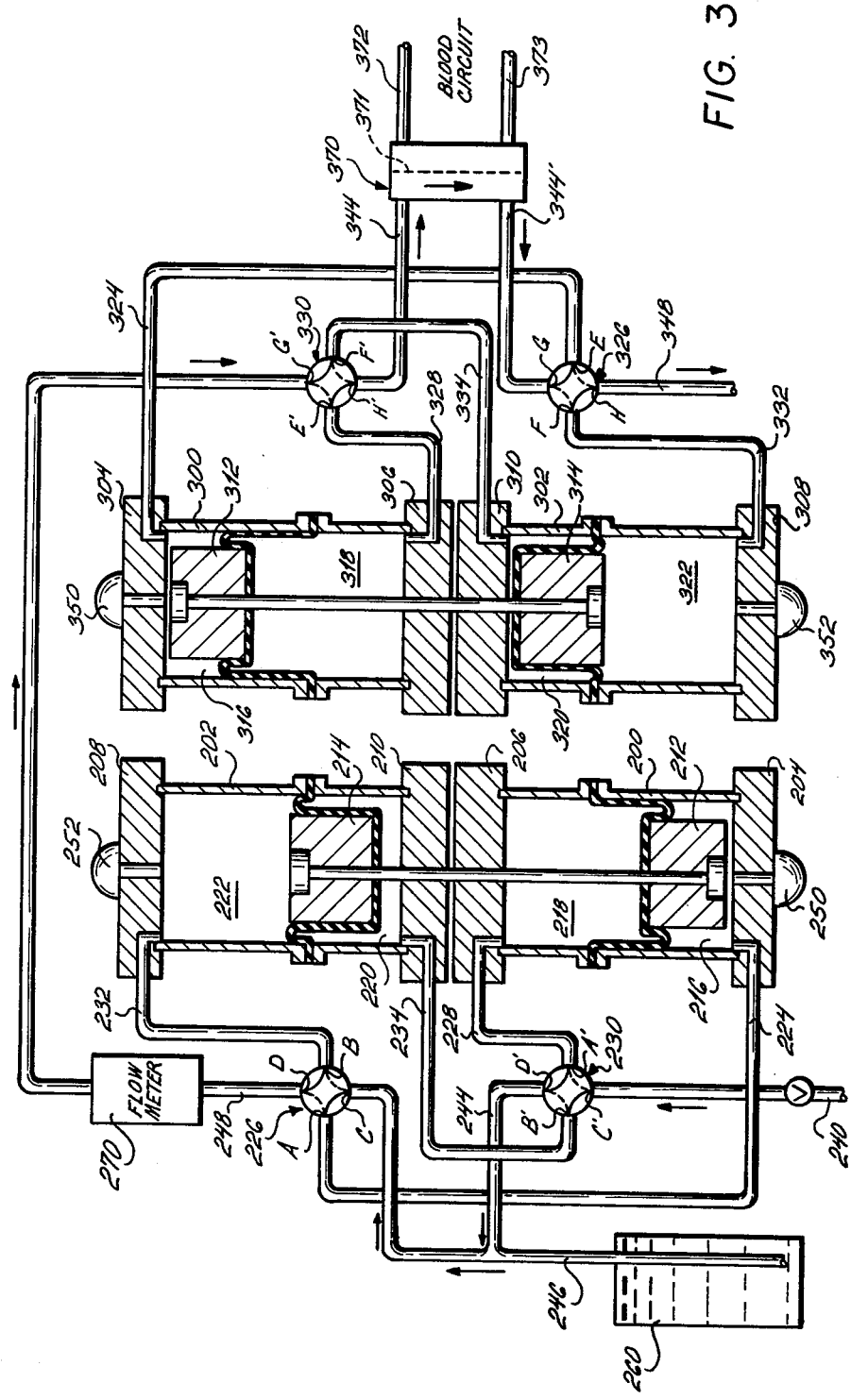
FIG. 3 shows, schematically, another embodiment of this invention.

In FIG. 3, there is shown an arrangement, in many respects resembling that of FIG. 2, but in which there are two units each constituted of two pistons and two cylinders. To distinguish clearly between the embodiments of FIG. 2 and FIG. 3, parts of the apparatus of FIG. 3 are identified by different reference numerals from those utilized in the embodiment of FIG. 2.

The left hand piston/cylinder units of FIG. 3 comprises a lower cylinder 200 and an upper cylinder 202. The ends of cylinder 200 are closed by port plates 204 and 206 and those of cylinder 202 are closed by port plates 208 and 210.

Disposed within cylinders 200 and 202 are pistons 212 and 214, respectively, each provided with a conventional rolling diaphragm seal so that cylinder 200 is divided into chambers 216 and 218 at opposite ends of the piston 212 and cylinder 202 is divided into chambers 220 and 222 to each side of piston 214. It is to be noted that the pistons are joined by a common piston rod guided in port plates 206 and 210.

Leading from chamber 216 through port plate 204, conduit means 224 communicates with port A of a four port valve 226 and conduit 228 leads to port A' of a four port valve 230 from chamber 218, through port plate 206.

Conduit 232 leads to port B of valve 226 from chamber 222 through port plate 208 and conduit 234 communicates between chamber 220 of cylinder 202 and port B' of valve 230.

A first fluid inlet conduit 240 extends from a pressurized supply of dilution water for the dialysate concentrate to port C' of valve 230. Conduit 244 communicates between port D' of valve 230 and port E of valve 226, conduit 244 including a T having a branch 246 communicating with a dialysate concentrate supply 260.

The valve 226 also includes a port D communicating with conduit 248 which communicates through a flow meter 270 with the hereinbelow described right hand piston/cylinder units.

Disposed in port plates 204 and 208 are proximity switches 250 and 252, respectively.

The right hand piston/cylinder units of FIG. 3 comprise an upper cylinder 300 and a lower cylinder 302. The ends of cylinder 300 are closed by port plates 304 and 306 and those of cylinder 302 are closed by port plates 308 and 310.

Disposed within cylinders 300 and 302 are pistons 312, and 314, respectively, each provided with a conventional rolling diaphragm seal so that cylinder 300 is divided into chambers 316 and 318 at opposite ends of the piston 312 and cylinder 302 is divided into chambers 320 and 322 to each side of piston 314. It is to be noted that the pistons are joined by a common piston rod sliding in port plates 306 and 310.

Leading from chamber 316 through port plates 304, conduit means 324 communicates with port E of a four port valve 326 and conduit 328 leads to port E' of a four port valve 330 from chamber 318, through port plate 306.

Conduit 332 leads to port F of valve 326 from chamber 322 through port plate 308 and conduit 334 communicates between chamber 320 of cylinder 302 and port F' of valve 330.

Conduit 248, conducting dialysate solution prepared in the other unit, extends through the flow meter 270 to port G' of the valve 330. Conduit 344 communicates between port H' of valve 330 and the inlet of the waste side of a dialysis cell 370 provided with a semi-permeable membrane 371. At the other side of the membrane 371, blood is conducted from and back to a patient through respective conduits 372 and 373. Conduit 344' communicates with the outlet of the waste side of the dialysis cell 370 and port G of valve 326.

The valve 326 also includes a port H communicating with conduit 348 which leads to an outlet for the mixture of dialysate solution and waste fluid.

Disposed in port plates 304 and 308 are proximity switches 350 and 353, respectively.

The operation of the system of FIG. 3 is as follows:

In the position shown in the drawings, i.e., with the pistons of the left hand piston/cylinder units at the lowermost point in their respective cylinders, port C' of valve 230 is connected to port B' and port A' is connected to port D'. In valve 226, port C is connected to port A and port B is connected to port D.

It is to be appreciated that the position of the valves 226 and 230 is to be controlled by solenoids actuated by one or other of switches 250, 252 in this embodiment shown as proximity switches, but obviously of any type compatible with the role of those switches, as pointed out hereabove.

In the meantime, water for diluting the dialysate concentrate supplied under adequate pressurization to constitute the water as a motive fluid for the piston/cylinder units will be passed along conduit 240 to valve 230 where it will move from port C' to port B' and through line 234 to chamber 220 of the cylinder 202.

Considering cylinder 200, as the piston 212 begins its movement from bottom to top, fluid contained in chamber 218 passes through ports A' and D' of valve 230, along conduit 244, through ports C and A of valve 226 and along conduit 224 to chamber 216 and, since the volume of fluid displaced from chamber 218 is lesser than that required to fill chamber 216, the excess volume will be made up by the dialysate concentrate drawn from the concentrate supply 260 through the conduit 246.

At the same time, fluid in chamber 222 will be moved from that chamber to line 232 and via ports B and D of valve 226 to line 248, through a flow meter 270 and to the fluid circuit including the other piston/cylinder units. The fluid from chamber 222 will comprise a precise mixture of predetermined proportions of the dialysate concentrate and dilution water constituting a dialysate solution of proper concentration for hemodialysis.

As the pistons 212 and 214 approach the extreme top position, proximity switch 252 will be activated to cause appropriate solenoids, not shown in the drawings, to shift the positions of valves 226 and 230 so that the dilution water will pass along conduit 240 from port C' to port A' of valve 230 to enter chamber 218, providing the motive force to shift the pistons from top to bottom. Fluid in chamber 216, as described hereinbefore, a predetermined mixture of the dialysate concentrate and dilution water, will be moved along conduit 224 to pass from port A to port D of valve 226 and along outlet 248 leading to the other unit. Similarly, fluid in chamber 220 will be moved along conduit 234 to pass from port B' to port D' of valve 230 and along conduit 244 to pass from port C' to port B' of valve 226 and enter along conduit 232, chamber 222. Since the volume of that fluid is lesser than that required to fill chamber 222, the excess will be made up by the dialysate concentrate drawn in through inlet 246.

As the device continues to operate, a substantially constant flow of dialysate solution of a predetermined concentration suitable for use in hemodialysis will flow out through the line 248.

Turning now to the right hand piston/cylinder units, in the position shown in the drawings, i.e., with the pistons of the right hand piston/cylinder units at the uppermost point in their respective cylinders, port G' of valve 330 is connected to port F' and port E' is connected to port D'. In valve 326, port G is connected to port E and port F is connected to port H.

In the meantime, dialysate solution supplied through conduit 248 under adequate pressurization to constitute the solution as a motive fluid for the piston/cylinder units will be passed along to valve 330 where it will move from port G' to port F' and through line 334 to chamber 320 of the cylinder 302.

Considering cylinder 300, as the piston 312 begins its movement from top to bottom, fluid contained in chamber 318 passes through ports E' and H' of valve 330, along conduits 344 and 344', through ports G and E of valve 326 and along conduit 324 to chamber 316 and, since the volume of liquid displaced from chamber 318 is lesser than that required to fill chamber 316, the excess volume will be made up by the waste fluids drawn through the membrane 371 to the dialysate side of the dialysis cell 370 and therefrom to the conduit 344'. It will be understood that the membrane 371 functions as an inlet for the waste fluid into the proportioning system of the invention.

At the same time, liquid in chamber 322 will be moved from that chamber to line 332 and via ports F and H of valve 326 to line 348 from which the liquid is discharged. The liquid from chamber 322 will comprise a precise mixture of predetermined proportions of the dialysate solution and waste fluid.

As the pistons 312 and 314 approach the extreme bottom position, proximity switch 352 will be actuated to cause appropriate solenoids, not shown in the drawings, to shift the positions of valves 326 and 330 so that the dialysate solution will pass along conduit 248 from port G' to port E' of valve 330 to enter chamber 318, providing the motive force to shift the pistons from bottom to top. Liquid in chamber 316, as described hereinbefore, a predetermined mixture of the dialysate solution and waste fluid, will be moved along conduit 324 to pass from port E to port H of valve 326 to line 348 from which the liquid is discharged. Similarly, liquid in chamber 320 will be moved along conduit 334 to pass from port F' to port H' of valve 330 and along conduits 344 and 344' to pass from port G to port F of valve 326 and enter along conduit 332, chamber 322. Since the volume of that liquid is lesser than that required to fill chamber 322, the excess will be made up by the waste fluid drawn in through the membrane 370 and to the conduit 344'.

As the device continues to operate, a substantial flow of a mixture of predetermined proportions of dialysate solution and waste fluid will issue from line 348 to be discarded.

The apparatus of FIG. 3, like the apparatuses of FIGS. 1 and 2, is subject to modifications, exemplary ones of which have been mentioned hereabove in connection with FIGS. 1 and 2, which do not deviate from the scope of the invention as defined in the appended claims.

Figure 4:
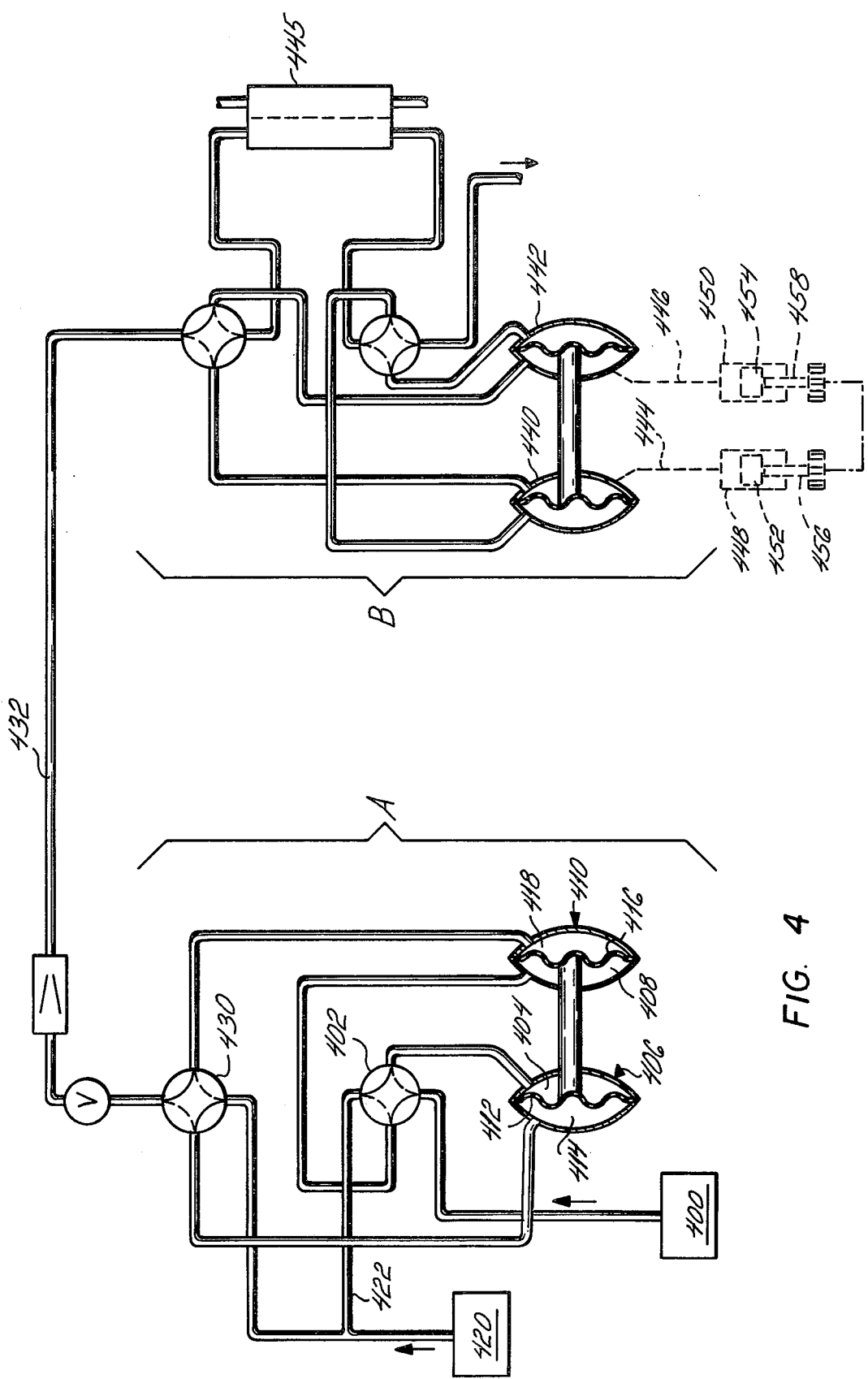
FIG. 4 shows, schematically, a still further embodiment of the invention.

The embodiment of the invention in FIG. 4 is, in operation, substantially similar to that of FIG. 3 and for this reason a detailed description of that operation is not repeated here, only the difference between the two embodiments being enumerated.

The primary difference resides in the fact that instead of piston/cylinder units, simple receptacles each divided into two chambers by a flexible disphragm are provided.

In FIG. 4 there is provided a supply 400 of diluent delivered alternately through four port valve 402 to chambers 404 and 408, respectively, of receptacles 406 and 410, receptacles 406 and 410 being divided by flexible diaphragm elements 412 and 416 respectively into chambers 404 and 414 and 418.

A source 420 of second liquid, in this case dialysate concentrate, is connected to conduit 422 which forms a part of the connection, as described with reference to FIG. 3, between chamber 404 and chamber 414 of receptacle 406 and between chamber 408 and chamber 418 of receptacle 410.

The dialysate solution is mixed in that connection and from receptacles 406 and 410 passes through four port valve 430 to the connection 432 between solution mixing system A and the dialyzing system indicated generally at B. The operation of the system B is largely similar to the corresponding parts of the system of FIG. 3 comprising instead of pistons and cylinders receptacles 440 and 442 of generally similar structure to receptacles 406 and 410 of system A. System B of course comprises a dialysis cell 446. To allow for adjustment of the withdrawal rate of the blood wastes, the lesser chambers of receptacles 440 and 442 may be provided with connections 444 and 446 which lead to respective ones of cylinder elements 448 and 450. Each of cylinder elements 448 and 450 is provided with a plunger element 452 and 454, respectively, which cooperate with ganged adjustable stop means 456 and 458, respectively, which cooperate with the plungers to limit a displacement of those plungers within the cylinders. It will be appreciated that by adjusting the limit of movement of the plungers the volumetric differential between the two chambers of receptacles 440 and 442 is effectively adjusted so that any ratio of blood waste withdrawal rate to dialysis solution flow from zero to design maximum can be obtained. It will be appreciated that where adjustment is made to render that differential zero an outlet from the system for wastes which will migrate across the membrane of the cell must be provided, that outlet delivering to a measuring vessel at which a record can be made of the quantity of blood wastes passed. Further, such an outlet must be provided in an arrangement in which the difference in volumes of the chambers is lesser than that volume of blood wastes which will migrate by osmosis across the cell. The outlet may, of course, be provided with a one-way valve.

It will be recognized that the structure of FIG. 4 is subject to similar variation to those described with reference to the preceding figures of the drawings and additionally it and the other embodiments of the invention are subject to various modifications described in my patents U.S. Pat. Nos. 4,037,616 and 4,054,522, as well as in my copending application Ser. No. 645,747.

What is claimed is:

1. In a hemodialysis system including a dialyzer cell having a membrane, means for conducting blood from a patient to one side of the membrane and means for conducting a dialysate past the other side of the membrane for withdrawing waste from the blood across the membrane and into the dialysate, improved means for controlling and monitoring volumetric waste withdrawal rate comprising an hydraulic circuit including a receptacle, a reciprocable partition within said receptacle and dividing the receptacle into two chambers, means reducing the effective volume swept by the partition in one chamber to be lesser than the volume swept by the partition in the other chamber, first conduit means constituting an inlet for the dialysate to said one chamber and connectable to a source of the dialysate, second conduit means connecting said one chamber to said other chamber and including the dialysis cell, third conduit means connected to the other chamber and constituting an outlet for dialysate mixed with waste, whereby the waste is caused to be drawn across the membrane in a volume directly related to the difference in effective volumes swept by the partition.

2. A system as claimed in claim 1 wherein said receptacle comprises a cylinder and said partition, a piston, said means reducing the effective volume swept by said piston in said one chamber comprising a piston rod extending from the piston and through said one chamber.

3. A system as claimed in claim 1 wherein said dialyzer cell is disposed in said second conduit means.

4. A system as claimed in claim 1 wherein said source of said dialysate is pressurized, said dialysate constituting a motive fluid for driving said piston in a direction to expand said one chamber.

5. A system as claimed in claim 1 wherein said source of said dialysate includes a pump.

6. A system as claimed in claim 1 wherein said source of said dialysate includes a regulating valve constituting means establishing the velocity of said piston movement in a direction to expand said one chamber.

7. A system as claimed in claim 1 wherein resilient means are provided to move said piston in a direction to expand said other chamber.

8. A system as claimed in claim 1 wherein a regulating valve is provided in said second conduit constituting means to establish the velocity of said piston movement in a direction to expand said other chamber.

9. A system as claimed in claim 1 wherein a flow meter is disposed in one of said conduit means, said flow meter being graduated to indicate the flows of dialysate solution and blood wastes.

10. A system as claimed in claim 1 wherein said first and second conduit means include a common connection to said one chamber, said common connection including valve means establishing communication alternatively between said first conduit and said one chamber and said second conduit and said one chamber.

11. A system as claimed in claim 1 wherein said second and said third conduit means include a common connection to said other chamber, said common connection including valve means establishing communication alternatively between said second conduit and said other chamber and between said third conduit and said other chamber.

12. A system as claimed in claim 1 including two axially aligned cylinders, each with a piston and each divided into two chambers, said pistons being interconnected by a piston rod constituting means reducing the effective volume swept by said pistons within the chambers in which said rod is disposed to be lesser than that of the other chambers, the lesser volume chamber of one cylinder expanding as the greater volume chamber of the other cylinder expands.

13. In a hemodialysis system including a source of a dialysate concentrate and a source of water for diluting the concentrate, improved means for proportioning the volumetric rate at which the concentrate is added to the dilution water relative to the volumetric flow rate of the dilution water, the proportioning means comprising a hydraulic circuit including a receptacle, a partition reciprocable in the receptacle and dividing the receptacle into two chambers, means reducing the effective volume swept by the partition in one chamber relative to the effective volume swept by the partition in the other chamber, first conduit means constituting an inlet for the dilution water to said one chamber and connectable to the source of the dilution water, second conduit means connecting said one chamber to said other chamber, third conduit means connected to said other chamber and constituting an outlet for the diluted dialysate concentrate, and fourth conduit means constituting an inlet for the dialysate concentrate and connectable between the source of the dialysate concentrate and the circuit to cause the concentrate to be added to the circuit in a volume directly related to the difference in effective volumes swept by the partition.

14. A system as claimed in claim 13 wherein said receptacle comprises a cylinder, said partition comprises a piston, said means reducing the effective volume swept by said piston in said one chamber comprises a piston rod extending from the piston and into said one chamber.

15. A system as claimed in claim 13 wherein said dialysate concentrate inlet comprises a connection into said second conduit means.

16. A system as claimed in claim 13 wherein said inlet for said dialysate concentrate communicates directly with said one chamber.

17. A system as claimed in claim 13 wherein said inlet for said dialysate concentrate communicates directly with said other chamber.

18. A system as claimed in claim 13 wherein said source of said dilution water is pressurized, said water constituting a motive fluid for driving said partition in a direction to expand said one chamber.

19. A system as claimed in claim 13 wherein said source of said dilution water includes a pump.

20. A system as claimed in claim 13 wherein resilient means are provided to move said piston in a direction to expand said other chamber.

21. A system as claimed in claim 13 wherein said first and second conduit means include a common connection to said one chamber, said common connection including a three port valve establishing communication alternatively between said first conduit and said one chamber and said second conduit and said one chamber.

22. A system as claimed in claim 13 wherein said second and said third conduit means include a common connection to said other chamber, said common connection including a three port valve establishing communication alternatively between said second conduit and said other chamber and between said third conduit and said other chamber.

23. A system as claimed in claim 13 wherein said second and said third conduit means include a common connection to said other chamber, said common connection including a three port valve establishing communication alternatively between said second conduit and said other chamber and between said third conduit and said other chamber.

24. A system as claimed in claim 13 including two axially aligned cylinders, each with a piston and each divided into two chambers, said piston being interconnected by a piston rod constituting means reducing the effective volume swept by said pistons within the chambers in which said rod is disposed to be lesser than that of the other chambers, the lesser volume chamber of one cylinder expanding as the greater volume chamber of the other cylinder expands.

25. A hemodialysis procedure which comprises connecting a patient to a blood side of a dialysis cell, establishing a closed, liquid filled system including a dialysate side of said dialysis cell, causing a dialysate solution to move in said system to the dialysate side of said cell at a first rate and simultaneously moving a fluid mixture from said dialysate side of the cell at a second and greater rate to cause blood wastes to be drawn from said blood side of the cell to the dialysate side of the cell at a rate to make up the difference in the rates at which dialysate is delivered to the cell and said fluid mixture is withdrawn from said cell, and controlling said difference between said rates of delivery and withdrawal, and wherein said dialysate solution is delivered to the cell from one chamber of the receptacle which is divided into two chambers by reciprocable partition means and said fluid mixture is withdrawn from the cell to the other chamber of said receptacle, said one chamber of said receptacle having means effective to reduce the volume swept by the partition means in said one chamber to be lesser than that swept in said other chamber.

26. In a hemodialysis system including a dialyzer cell having a membrane, means for conducting blood from a patient to one side of the membrane and means for conducting a dialysate past the other side of the membrane and withdrawing waste from the blood across the membrane into the dialysate including means for controlling and monitoring volumetric waste withdrawal rate comprising an hydraulic circuit including a receptacle, movable partition means dividing that receptacle into two chambers, a connection from one chamber to a dialysate side of the cell and from that side of the cell to the other chamber, means producing reciprocation of said partition within said receptacle alternately to expand and contract said chambers and means in one chamber effective to reduce the volume swept by the partition in said chamber to be lesser than that swept by the partition in the other chamber whereby waste is caused to be drawn across the membrane in a volume directly related to the difference in effective volumes swept by said partition.

27. The apparatus as claimed in claim 26 including means effective to adjust the difference in volumes of said chambers.

28. In a hemodialysis system including a dialyzer cell having a membrane, means for conducting blood from a patient to one side of the membrane and means for conducting a dialysate past the other side of the membrane for withdrawing waste from the blood across the membrane and into the dialysate, including means for controlling and monitoring volumetric waste withdrawal rate comprising an hydraulic circuit including a receptacle, reciprocable partition means within said receptacle and dividing that receptacle into two chambers, means for reciprocating said partition means within said receptacle alternately to expand and contract said chambers, an inlet for dialysate to one of said chambers, conduit means connecting said one chamber to said other side of said membrane and to said other chamber, a fluid outlet from said second chamber, valve means associated with said dialysate inlet, said outlet and said conduit means and operable to permit controlled reciprocation of said partition means, and means disposed in said one chamber effective to render the volume of dialysate solution delivered to said one chamber lesser than that volume required to fill the other chamber upon expansion of said other chamber whereby blood wastes are induced into said circuit in volumes equal to the difference in said aforementioned volumes.

29. The apparatus as claimed in claim 28 wherein said chambers are formed within a receptacle and are separated by reciprocable partition means, said partition means comprising a flexible diaphragm element.

30. The apparatus as claimed in claim 28 wherein said receptacle comprises a cylinder and said partition means comprises a piston reciprocable within said cylinder.

31. A hemodialysis system comprising a dialyzer cell, a closed, liquid filled hydraulic system having a first receiving chamber, a second receiving chamber, means connecting said chambers, said means connecting said chambers including a dialysate side of said cell, means transporting a predetermined volume of dialysate solution from said first chamber to said second chamber through said connecting means and means rendering the displacement volume of said second chamber greater than said predetermined displacement volume of dialysate solution whereby blood wastes are drawn from the blood side to the dialysate solution side of said cell to fill, with a mixture of said blood wastes and said dialysate solution, said second chamber, and wherein said chambers are formed within a receptacle and are separated by reciprocable partition means, said partition means comprising a flexible diaphragm element.

32. A hemodialysis system including a dialyzer cell having blood and dialysate solution sides comprising a closed, liquid filled hydraulic system comprising a first receiving chamber, a second receiving chamber, means connecting said chambers to said dialysate solution side of said cell, means transporting a predetermined volume of dialysate solution from said first chamber to said second chamber through said connecting means and means rendering the volume of said second chamber greater than said predetermined volume of dialysate solution whereby blood wastes are drawn from the blood side to the dialysate solution side of said cell to fill, with said solution, said second chamber, and wherein said chambers are formed within a receptacle and are separated by reciprocable partition means, said partition means comprising a flexible diaphragm element.

33. A hemodialysis procedure comprising causing a patient's blood to pass through a blood side of a dialysis cell, delivering a predetermined volume of dialysate solution to a first chamber to fill that chamber, making a connection from said first chamber to a solution side of said cell and from said solution side of said cell to a second and larger chamber and passing said volume of dialysate solution from said first chamber to said second chamber through said connection to cause blood wastes to be drawn across the cell from the blood side to the solution side thereof and be admitted to said second chamber in an amount equal to the difference of volumes of said chambers, and wherein said receptacle comprises a cylinder and said partition means comprises a piston reciprocable within said cylinder 34. A hemodialysis system comprising a dialyzer cell, a closed liquid filled hydraulic system having a first receiving chamber, a second receiving chamber, means connecting said chambers, said means connecting said chambers including a dialysate side of said cell, means transporting a predetermined volume of dialysate solution from said first chamber to said second chamber through said connecting means and means rendering the volume of said second chamber greater than said predetermined volume of dialysate solution whereby blood wastes are delivered to the dialysate side of cell to fill, with said dialysate solution, said second chamber, said chambers being formed with a receptacle and being separated by reciprocable partition means said receptacle comprising a cylinder and said partition means comprising a piston reciprocable within said cylinder.

35. A hemodialysis system including a dialyzer cell having blood and dialysate solution sides comprising a closed liquid filled hydraulic system comprising a first receiving chamber, a second receiving chamber, means connecting said chambers to said dialysate solution side of said cell, means transporting a predetermined volume of dialysate solution from said first chamber to said second chamber through said connecting means and means rendering the volume of said second chamber greater than said predetermined volume of dialysate solution whereby blood wastes are drawn from the blood side to the dialysate solution side of said cell to fill, with said solution, said second chamber, and wherein said chambers are formed within a receptacle and are separated by reciprocable partition means and wherein said receptacle comprises a cylinder and said partition means comprises a piston reciprocable within said cylinder.

36. A hemodialysis procedure comprises causing a patient's blood to pass through a blood side of a dialysis cell, delivering a predetermined volume of dialysate solution to a first chamber to fill that chamber, making a connection from said first chamber to a solution side of said cell and from said solution side of said cell to a second and larger chamber and passing said volume of dialysate solution from said first chamber to said second chamber through said connection to cause blood wastes to be drawn across the cell from the blood side to the solution side thereof and be admitted to said second chamber in an amount equal to the difference in volumes of said chambers, and wherein said chambers are formed within a receptacle and are separated by reciprocable partition means and wherein said receptacle comprises a cylinder and said partition means comprises a piston reciprocable within said cylinder.

37. A hemodialysis procedure which comprises connecting a patient to the blood side of a dialysis cell, passing a known volume of dialysate solution through the dialysate side of said dialysis cell, from one side of a closed, liquid-filled hydraulic system to another side of said system while controllably increasing the internal volume of said hydraulic system to cause blood wastes to be drawn to the dialysate side of the cell in direct volumetric relationship to said increase in volume of said hydraulic system, and wherein said dialysate is passed through said dialysate side of said cell from one chamber of a closed receptacle, which is divided into two chambers by reciprocable partition means, to the other chamber of said receptacle, said one chamber of said receptacle having means effective to increase the volume of said closed, liquid-filled hydraulic system as said dialysate solution is being passed from said one chamber to said other chamber of said receptacle.

* * * * *